United States Patent [19]

Tannenbaum et al.

[11] 3,968,009

[45] *July 6, 1976

[54] PROCESS FOR REDUCING NUCLEIC ACID CONTENT OF YEASTS AND BACTERIA

[75] Inventors: Steven R. Tannenbaum, Framingham; Anthony J. Sinskey, Boston, both of Mass.; Stephen B. Maul, Flemington, N.J.

[73] Assignee: Massachusetts Institute of Technology, Cambridge, Mass.

[ * ] Notice: The portion of the term of this patent subsequent to Mar. 13, 1990, has been disclaimed.

[22] Filed: May 19, 1975

[21] Appl. No.: 578,772

Related U.S. Application Data

[63] Continuation-in-part of Ser. No. 340,022, March 12, 1973, abandoned, which is a continuation-in-part of Ser. No. 53,263, July 8, 1970, Pat. No. 3,720,585.

[52] U.S. Cl............................... 195/98; 195/28 N; 195/82; 195/96; 426/62
[51] Int. Cl.² ......................................... C12C 11/00
[58] Field of Search................. 195/28 R, 28 N, 82, 195/98, 96

[56] References Cited

UNITED STATES PATENTS

| 3,139,385 | 6/1964 | Ogata et al. ..................... 195/28 N |
| 3,720,585 | 3/1973 | Tannenbaum et al............ 195/28 N |

OTHER PUBLICATIONS

Haight et al., J. of Bacteriology vol. 92 No. 2 pp. 1388–1393, Nov. 1966.

*Primary Examiner*—Alvin E. Tanenholtz
*Attorney, Agent, or Firm*—Arthur A. Smith, Jr.; Martin M. Santa; Anthony M. Lorusso

[57] ABSTRACT

Process for reducing nucleic acid content of yeasts and bacteria comprising heat shocking for a period of time and at a temperature selected to increase effectiveness of enzymes which break down nucleic acids without allowing proteins to break down or leak out of the cell, and incubating the heat-shocked cells at a temperature lower than the heat shock temperature under conditions in which the cells remain intact and nucleic acid fragments permeate the cell walls.

11 Claims, No Drawings

PROCESS FOR REDUCING NUCLEIC ACID CONTENT OF YEASTS AND BACTERIA

CROSS REFERENCE TO A RELATED APPLICATION

This application is a continuation-in-part of application Ser. No. 340,022, filed Mar. 12, 1973 entitled Edible Yeast-like Substances and Process for Reducing the Nucleic Acid Content of Yeast-like Substances, now abandoned, which is a continuation-in-part of application Ser. No. 053,263, filed July 8, 1970, entitled "Process of Reducing the Nucleic Acid Content of Yeast," now U.S. Pat. No. 3,720,585.

BACKGROUND OF THE INVENTION

Two problems which in the past have prevented the use of yeasts or bacteria as a food for human consumption are their high nucleic acid content and unacceptable palatability.

During metabolism in humans, nucleic acid breaks down to uric acid and therefore presents potential problems to human health, especially when large amounts are present in the blood stream. High uric acid content in blood is associated with diseases such as gout and tophi and with the formation of uric acid stones in the urinary tract. In order to use single-cell proteins such as yeasts and bacteria as a primary protein source for human population, the nucleic acid content obviously must be reduced to levels which are safe for human consumption. In this regard, a maximum level of nucleic acid intake is in the range of two grams of nucleic acid per day.

A procedure for degrading nucleic acids from unicellular organisms is through heat-shocking. (see e.g. R. D. Haight et al., *Journal of Bacteriology*, Nov. 1966, p. 1388). When an organism is placed in a thermal environment even slightly above its maximal growth temperature for any extended period of time, it soon dies and releases substantial portions of its nucleic acid. Unfortunately, this method is unsuitable for preparing high protein food products, since it simultaneously induces protein loss at a rate greater than or equal to loss of nucleic acids.

Ogata et al., in U.S. Pat. No. 3,139,385 disclose a method of producing nucleotides from living unicellular organisms by incubating them in an alkaline solution for 10 to 72 hours at a temperature of about 25° to 30° centigrade. Eighty to one-hundred percent of the intracellular nucleic acid disappears with this process, but the remaining product is not suitable for human consumption.

As set forth above, another problem associated with yeasts and bacteria as a protein source is their poor palatability. For example, yeast ordinarily has a sharp, pungent, salty taste. For this reason, if it is used as a protein supplement (in foods such as cereals, simulated milk, and grain), the natural flavor of the material to which the protein is added is substantially altered making the food undesirable or unpalatable.

Prior to the advent of the process disclosed in parent patent application Ser. No. 053,263, filed July 8, 1970, (now U.S. Pat. No. 3,720,585) entitled "Process for Reducing the Nucleic Acid Content in Yeast," the teachings of which are incorporated herein by reference, no truly acceptable method for reducing the nucleic acid content in yeast-like substances or bacteria were known which would simultaneously preserve their protein food value and enable the treated substance to be safely used as a palatable food source suitable for human consumption.

In addition to the specific yeast-like substances which are disclosed in U.S. Pat. No. 3,720,585 as being treatable by that process to render them edible, in accordance with the present invention, it has been discovered that bacteria such as the bacterium *Bacillus subtillus* and yeasts such as the strain of yeast known as *Saccharomyces cerevisiae* can be similarly treated to reduce the nucleic acid content thereof and produce a heretofore unknown food product.

SUMMARY OF THE INVENTION

The nucleic acid content of yeast-like substances is reduced in accordance with the present invention by a process which includes heat shocking for a time and at a temperature insufficient to release any substantial amounts of protein or nucleic acid followed by incubation at a controlled pH for prescribed intervals of time to produce an edible, bland, high protein product.

Accordingly, it is an object of the invention to provide a process by which previously known protein sources, such as yeasts and bacteria are rendered edible by reducing their nucleic acid content without reducing their protein content.

A further object of the invention is to provide a process by which the health problems associated with eating yeast and yeast-like substances, such as bacteria, are eliminated.

A further object of the present invention is to provide a process by which the taste of yeast-like substances is made palatable.

A further object of the present invention is to provide a process for reducing the nucleic acid content of the bacterium *Bacillus subtilis* and of the strain of yeast known as *Saccharomyces cerevisiae*.

Another object of the present invention is to provide a process for removing nucleic acid from yeast-like substances.

Yet another object of the present invention is to provide the strain of yeast known as *Saccharomyces cerevisiae* with a nucleic acid content of less than 3 percent of the weight of the dry substance.

DESCRIPTION OF THE PREFERRED EMBODIMENTS

The present process produces a bland, neutral tasting, yeast-like substance not readily discernible as such when mixed with other foods and which is high in protein and safe for human consumption. Broadly, the process includes the step of heat shocking the cells to be treated followed by the step of incubating the heat-shocked cells under appropriate conditions to produce a substance with a reduced nucleic acid content and a bland, neutral, highly palatable taste. Although the mechanism by which the nucleic acid is removed from the cells is not completely understood, a probable mechanism is that the initial heat shock partially unfolds the nucleic acid molecules inside the cell and/or destroys enzyme inhibitors, thereby allowing the ribonucleases (the enzymes inside the cells) to break down these nucleic acids more easily, since the structure of the nucleic acids is now unfolded and easily acted upon. Also, heat shocking may activate the enzymes inside the cells so as to make them more efficient in the breakdown of the nucleic acids. In accordance with the present invention, it has been discovered that too high a heat shocking temperature for too short a period of time is ineffective, if the temperature is high enough to inactivate the enzymes. Furthermore, too low a temperature is not high enough to achieve the initial unfolding of the nucleic acids. Hence, a proper temperature range and time selected to unfold the nucleic acids and to maintain te activity of the enzymes inside the cell without rupturing the cell walls during the heat-shocking step is critical.

Because enzymes act upon nucleic acid and break it down into smaller structural units (neclecocides and nucleotides of comparatively low molecular weight), these smaller units can readily leak from the cells into te surrounding medium. Thus, in the incubation step, the cells sit at a comfortable temperature and the nucleic acid fragments, having comparatively low molecular weights, permeate through the cell membrane and out of the cell.

It is important to note that the process can be accelerated by adding or removing certain ions from the incubation media which are known to enhance the activity of ribonucleases and hence increase nucleic acid breakdown. Such ions are sodium, potassium, magnesium, calcium and manganese. The manner of adjusting the ion content is well known to those skilled in the art and will not be discussed further.

At this point, it should be noted that it is well known that losses of ribonucleic acid (RNA) occur upon injury to cells by drying conditions or exposure to certain adverse environmental factors such as radiation or heating. Also, as previously indicated, processes for extracting ribonucleic acid from cells for the purpose of utilizing the ribonucleic acid are known; however, the known prior art processes for removing nucleic acid from cells are not considered satisfactory if an edible high protein food is desired. The reason why the present process is superior to the prior art processes in terms of producing an edible food is that during the treatment of the present invention, i.e. heat shocking and incubation, the temperature and other conditions are such that the cell walls are not ruptured. Because the cell walls are maintained intact, the nucleic acid fragments can leak through the cell walls and the protein can not. In connection with the foregoing an important aspect of the present invention is that the heat shocking temperature is selected so that protein neither breaks down or leaks out of the cell while nucleic acid does break down and is allowed to leak out of the cell. Thus, the present process for reducing the content of nucleic acid in cells is a marked advance over the prior art because it produces a neutral and bland-tasting substance with a reduced nucleic acid content, yet a high protein content, which can be added easily and safely to foods without changing their natural flavors. The newly developed substances according to the principle of the present invention offers human population an inexpensive protein (up to 50 percent by weight) which may be used as supplement to such foods as flavored drinks and cereals. Indeed, the new substances may be used as a primary protein source. Futhermore, land need not be utilized in order to produce this protein source. Another use for this protein is as an animal feed. The process and product of the present invention is further illustrated by the following examples.

EXAMPLE 1

Bacillus subtilis ATCC 6051 bacteria were grown in continuous culture on the medium of A. L. Demain (Journal of Bacteriology, 75 517–22, 1958) containing added glucose as the carbon source and L-glutamic acid to stimulate optimal growth. Temperature growth was 30°C and pH was controlled at 6.0. The initial nucleic acid content of the cells under these conditions was measured at approximately 19 percent by weight. After collection, the cells were treated in accordance with the present invention.

The first step in the process, heat shocking, was performed by passing a suspension of Bacillus subtilis and spent medium through a 56 centimeter length of 1/32 inch stainless steel tubing, immersed in a vigorously stirred water bath at the specified temperature. The conditions for this heat-shocking step were a temperature of 68°C and a nominal residence time of 4–6 seconds. Under these conditions, the bulk temperature of the cells is within 1°C of bath temperature after about one second in the heat exchanger. After heat shocking, the cells were either incubated immediately or were held at zero degrees C until the incubation treatment was performed.

The second step in the process, incubation, was performed by maintaining the heat-shocked cells at 52.5°C for two hours. In some cases, the pH of the surrounding incubation medium was adjusted and held constant during the incubation period. The various cell treatments are described as follows:

a. Control — no treatment, cells held at zero degrees C
b. Heat-shocked and 2 hour incubation at 52.5°C
c. Heat-shocked, pH of cell suspension adjusted to 5.0, 2 hour incubation at 52.5°C
d. Heat-shocked, pH of cell suspension adjusted to 8.0, 2 hour incubation at 52.5°C The results of these different treatments are given in the following table.

| Treatment | Nucleic Acid % Dry Weight | Protein % Dry Weight |
|---|---|---|
| (a) | 17.7 | 40 |
| (b) | 15.7 | 54 |
| (c) | 21.0 | 53 |
| (d) | 6.0 | 57 |

The heat-shock step does not in itself lead to nucleic acid reduction but must be followed by an incubation step at the appropriate condition. In the case of Bacillus subtilis, this condition is a pH of 8.0. The heat-shock activates the endogenous ribonuclease which is active at pH 8.0 but not at 5.0 or 6.0. In general, the proper set of incubation conditions must be selected for each organism.

EXAMPLE 2

Saccharomyces cerevisiae, strain A364A, was employed in this example. Saccharomyces cerevisiae strain A364A is a haploid yeast designated (a). This haploid strain was mated with Saccharomyces cerevisiae strain 79-20-30c($\alpha$) and the resulting diploid strain of Saccharomyces cerevisiae was also investigated. In addition to the above mentioned strains of Saccharomyces cerevisiae, commercial Baker's yeast obtained as a moist cake was studied both as received from the supplier and after cultivation in the laboratory.

All of the strains of yeast were cultivated in 25 ml of YDPA broth in a 250 ml Erylenmeyer flask at 30°C on a rotary shaker (250 rpm) for 24–30 hours. YDPA is a standard medium for the cultivation of yeast and contains 1 percent Bacto Yeast extract, 2 percent peptone, 2 percent glucose and 0.003 percent adenine-sulfate. The Baker's yeast obtained from the commercial supplier as a moist cake was re-suspended in YDPA medium to a final cell concentration equivalent to that obtained with the strains propagated in the laboratory.

The first step in the process was performed by passing a suspension of the various yeast strains in spent medium through a stainless steel coil 56 centimeters in length and 1/32 in diameter immersed in a vigorously stirred water bath at the specified temperature. The conditions for this first step were a temperature of 68°C and a nominal residence time of 4–6 seconds. Under these conditions, the bulk temperature of the cells is within 1°C of bulk temperature after about one second in the heat exchanger. After heat shocking, the cells were incubated immediately or were held at 0° centigrade until incubation.

The second step in the process (incubation) was performed by maintaining the heat-shocked cells at 52.5° centigrade for two hours. In some cases, the pH of the surrounding incubation medium was adjusted and held constant during the incubation period. The various treatments may be summarized as follows:

*Saccharomyces cerevisiae* strains studied with the abovedescribed heat-shock procedure are:
 a. *Saccharomyces cerevisiae* strain A364A(a)
 b. *Saccharomyces cerevisiae* (diploid from A364A(a)/79-20-30C($\alpha$)
 c. Commercial Baker's yeast
 d. Baker's yeast laboratory cultivated The results of these treatments of these strains by the heat-shock procedure are compared to untreated yeast cells in the following table.

| Cell Strain | pH During Incubation | Nucleic Acid % Dry Weight | Protein % Dry Weight |
|---|---|---|---|
| a) | 5.0 | 6.63 | 45.7 |
| a') | 5.0 | 2.7 | 56.8 |
| b) | 4.6 | 7.3 | 47.0 |
| b') | 4.6 | 6.9 | 48.0 |
| c) | 5.0 | 7.11 | 48.9 |
| c') | 5.0 | 6.55 | 49.4 |
| d) | 4.5 | 7.31 | 50.56 |
| d') | 4.5 | 6.89 | 51.90 | a, b, c, and d = untreated
a', b', c', and d' = treated (heat shock, 68°C followed by incubation at 52.5°C for two hours).

With *Saccharomyces cerevisiae* there is a variability in the susceptibility of the yeast to the heat shocking and incubation steps. It appears that haploid strains are more sensitive than diploid strains to the process which indicates that the amounts of an endogenous ribonuclease are under genetic control which influences the response of cells to the process of the present invention.

In co-pending application Ser. No. 053,263 entitled "Process of Reducing the Nucleic Acid Content in Yeast," heat shocking and incubation conditions are disclosed for reducing the nucleic acid content of *Candida utilis* and *Candida intermedia*. Typical examples setting forth the process parameters for reducing the nucleic acid content of these yeasts is given below in Examples 3-5.

EXAMPLE 3

*Candida utilis* yeast was grown in continuous culture on the defined basal medium of Miller and Johnson [1] with glucose as the carbon source and at a pH of 4 with a suitable nitrogen source such as ammonia. The initial nucleic acid content of the cells under these conditions was measured at approximately 7 percent. After collection, the cells were treated in accordance with the present invention.

1. See, Miller T. L. and Johnson M. T., Biotech. BioEng., Vol. 8, p. 549. (1966).

The first step of heat shocking the cells was performed by passing a suspension of *Candida utilis* and spent medium through a 56 centimeter length of 1/32 inch stainless steel tubing, immersed in a vigorously stirred water bath at the specified temperature. To optimize the process steps, a nominal residence time of 5.5 to 6 seconds and a temperature of 68°C were chosen for heat shocking the cells. Under these conditions, the bulk temperature of the cells is within 1°C of bath temperature after about one second in the heat exchanger. After heat shocking the cells, they were collected at 0° C or were incubated immediately first at 45°–50°C at a pH of 4½ to 7. The method of collection does not affect the final results. Incubation was completed by heating two ml samples in 13 × 100 mm pyrex tubes for 10 minutes to infinity in a water bath at 50 to 60°C at a pH of 4½ to 7. After harvesting, the cells were washed once with water. The yeast cells had a nucleic acid content of 1 to 1.5 percent (and approximately 50 percent protein) as opposed to the original 7 percent nucleic acid content. Moreover, the resulting yeast had a bland, neutral, highly palatable taste.

EXAMPLE 4

First, an initial heat shock on *Candida utilis* is applied as described in Example 3. The heat-shocked substance is incubated in one step at a temperature of 50° to 55°C for 10 minutes to an infinitely long time. The most appreciable effects are achieved within an hour.

The results achieved by this process with a single step incubation are similar to those achieved with a process with a two-step incubation as described in Example 3.

EXAMPLE 5

*Candida intermedia* was heat shocked (as was the *Candida utilis* as in Example 3) at 68°C for from 5 to 6 seconds. During incubation, the temperature was reduced in a single step to 52.5°C for from two to three hours. The acid level of the material was thereby reduced from between 7.5 percent and 8 percent dry weight to 1.5 percent dry weight.

EXAMPLE 6

The effectiveness of the process of the present invention has been demonstrated by measuring the protein/nucleic acid ratio in various organisms in their natural, untreated state, and comparing this ratio with the protein/nucleic ratio after treatment in accordance with the process of the present invention. The results are summarized in the following table:

| Organism | Protein/nucleic acid natural state | after treatment |
|---|---|---|
| *Candida lipolytica* NRRL-Y-323 | 10.4 | 75 |
| *Candida lipolytica* NRRL-Y-1094 | 13.1 | 100 |

-continued

| Organism | Protein/nucleic acid natural state | after treatment |
|---|---|---|
| Candida lipolytica NRRL-Y-37-1 | 8.3 | 70 |
| Candida lipolytica NRRL-Y-60-26 | 9.4 | 68 |
| Candida utilis NRRL-Y-900 | 6.5 | 42 |
| Saccharomycis cerivisiae A364A(a) | 6.9 | 21 |

Final protein contents are about 50 percent; final nucleic acids are usually between 0.5 – 2.5 percent but at times can approach 7 percent. Examination of material that leaked out of the cells indicated no loss of protein.

The significance of the foregoing is that with the present process nucleic acids break down and leak out of the cell; but, protein does not break down nor it is allowed to leak out of the cell. Further testing in accordance with the present invention has indicated that the steps of heat shocking followed by incubation can be used on a variety of unicellular substances to lower their nucleic acid content.

In connection with the term "yeast-like substance," as used throughout this specification and claims, the term "yeast-like substance," is intended to be generic to yeast and other unicellular organisms such as fungi and bacteria.

As is shown by the various examples above, parameters of temperature and duration of the treatment are critical to palability and necessary to optimize nucleic acid removal without simultaneously removing protein. In this regard, some experimentation in order to ascertain the optimum temperature and duration of temperature treatment during the heat-shocking step is required. For most cases, the temperature will be above the maximum viability temperature and usually between 60° and 70°C and the duration from 2 to 20 seconds. Duration and temperature should be chosen such that rupture of substantial numbers of cell walls is not induced. The important factor for one skilled in this art to consider when trying to determine the temperature and duration of treatment during the heat-shocking step is that the purpose of heat shocking the cells is to increase the ability of the enzymes inside the cells to break down te nucleic acids into smaller units. If the temperature is too high, the enzymes become inactive and the cell walls can rupture.

In accordance with the present invention, it has been affirmed that heat shocking unicellular organisms at a temperature which increases the ability of the enzymes inside the cells to break down the nucleic acid is critical. Although the temperature and duration of time for heat shocking varies from organism to organism, the determination of these parameters is well within the skill of those in this art once the general concept of heat shocking is revealed to them.

The pH of the cell growth medium during heat-shocking can vary widely. On the other hand, tests have indicated that in order to optimize nucleic acid removal during the incubation period, the selection of a proper pH is important. During the incubation period, the cells are treated at a temperature for a period of time which is comfortable for the cells but which permits nucleic acid fragments to permeate through the cell walls. Thus, in accordance with the present invention, unicellular organisms are subjected to a heat-shocking process to activate the endogenous ribonuclease, and the cells are then incubated for the time interval at a temperature and pH at which the ribonuclease remains active. The temperature utilized to incubate the cells is always lower than the temperature utilized to heat shock the cells.

From the foregoing examples, it should be noted that all yeast-like cells that are heat shocked and then incubated at a pH suitable for enzyme activity result in an organism with a reduced nucleic acid content. For some unicellular organisms, the reduction in nucleic acid content in accordance with the present invention is greater than for others; however, all cells treated under the proper conditions in accordance with the present invention showed some reduction in the percent of nucleic acid without substantial protein loss. As is shown by Example 1, improper pH adjustment during the incubation period can increase the percent of nucleic acid in the treated substance.

In accordance with the present invention, during the heat-shocking step, nucleic acids are made ready for breakdown. Subsequently, during incubation, these nucleic acids break into fragments and leak through the cell walls under conditions which allow the cells to remain intact. The process is highly attractive in that it inexpensively changes yeast to a more palatable and safer food without requiring extraneous chemicals. In this regard, in the present invention, the unicellular organisms are purged of a great portion of their nucleic acid while leaving those cells healthy and uncontaminated with extraneous chemicals.

By drastically reducing the nucleic acid content of yeasts and yeast-like substances in accordance with the principles of the present invention, well-known protein sources become available and safe for human consumption.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A process for reducing the nucleic acid content in a unicellular substance selected from the group of yeasts and bacteria comprising the steps of:
   heat shocking said unicellular substance for a period of time and at a temperature selected to increase the activity of enzymes inside the cells of said unicellular substance sufficiently to enable said enzymes to break down nucleic acids into smaller fragments, said heat shock being insufficient to rupture substantial numbers of cell walls or to induce protein to leak out of said cells; and,
   incubating cells which have been subjected to said heat-shocking step for a period of time and at a temperature which is lower than the temperature selected in said heat-shocking step, the temperature at which heat-shocked cells are incubated being a temperature at which the cells of said unicellular substances remain intact but at which nucleic acid fragments permeate the walls of said cells.

2. The process of claim 1 wherein the temperature selected for said heat shocking step is lower than that at which enzymes are inactivated.

3. The process as set forth in claim 2 wherein the cells are incubated in a medium at a pH at which the ribonuclease in the cells being treated remain active.

4. The process as set forth in claim 1 wherein the temperature utilized during the heat-shocking step activates the endogenous ribonuclease present in the cells and wherein, during the incubation step, the cells are incubated at a temperature at which ribonuclease remains active.

5. The process of claim 1 wherein said incubation is conducted at a pH which promotes migration of said nucleic acid fragments out of said cells.

6. The process of claim 1 wherein said group comprises strains of *Candida utilis*, *Candida intermedia*, *Bacillus subtilis*, haploid and diploid *Saccharomyces cerevisiae*, commerical baker's yeast, and *Candida lipolytica*.

7. The process of claim 1 wherein the temperature selected for said heat shocking step is above the viability temperature of said cells.

8. The process of claim 1 wherein the heat shocking step is effected by subjecting said unicellular substance to a temperature between 60° and 70°C for a period of from 2 to 20 seconds.

9. The process of claim 1 wherein the said unicellular substance comprises *Saccharomyces cerevisiae*, and wherein, during the heat shocking step, the unicellular substance is heated to a temperature of 68°C.

10. The process of claim 9 wherein said heat shocked unicellular substance is incubated at a temperature of 52.5°C.

11. The process of claim 10 wherein said heat shocked unicellular substance is incubated for 2 hours.

* * * * *